United States Patent
Simpson et al.

(10) Patent No.: US 9,743,871 B2
(45) Date of Patent: Aug. 29, 2017

(54) MULTIPLE ELECTRODE SYSTEM FOR A CONTINUOUS ANALYTE SENSOR, AND RELATED METHODS

(71) Applicant: Dexcom, Inc., San Diego, CA (US)

(72) Inventors: Peter C. Simpson, Encinitas, CA (US); Sebastian Bohm, San Diego, CA (US); Robert J. Boock, Carlsbad, CA (US); Matthew D. Wightlin, San Diego, CA (US); Huashi Zhang, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 694 days.

(21) Appl. No.: 13/789,371

(22) Filed: Mar. 7, 2013

(65) Prior Publication Data

US 2014/0088389 A1    Mar. 27, 2014

Related U.S. Application Data

(60) Provisional application No. 61/705,066, filed on Sep. 24, 2012.

(51) Int. Cl.
*A61B 5/05* (2006.01)
*A61B 5/1486* (2006.01)
(Continued)

(52) U.S. Cl.
CPC ........ *A61B 5/1486* (2013.01); *A61B 5/14532* (2013.01); *C12Q 1/002* (2013.01); *A61B 5/14865* (2013.01); *A61B 2562/125* (2013.01)

(58) Field of Classification Search
CPC combination set(s) only.
See application file for complete search history.

(56) References Cited

U.S. PATENT DOCUMENTS

2007/0151868 A1* 7/2007 Staib ................... A61B 5/1486
                                                        205/792
2008/0083617 A1* 4/2008 Simpson ............ A61B 5/14532
                                                        204/403.1

(Continued)

OTHER PUBLICATIONS

Palmisano, F., et al. "Simultaneous monitoring of glucose and lactate by an interference and cross-talk free dual electrode amperometric biosensor based on electropolymerized thin films." Biosensors and Bioelectronics 15.9 (2000): 531-539.*

*Primary Examiner* — Michael Kahelin
*Assistant Examiner* — Mitchell E Alter
(74) *Attorney, Agent, or Firm* — Knobbe Martens Olson & Bear, LLP

(57) ABSTRACT

In one embodiment, a continuous analyte sensor having more than one working electrode, and configured to reduce or eliminate crosstalk between the working electrodes. In another embodiment, a continuous analyte sensor having more than one working electrode, and configured so that a membrane system has equal thicknesses over each of the electrodes, despite having differing numbers of layers over each of the electrodes. In another embodiment, a configuration for connecting a continuous analyte sensor to sensor electronics. In another embodiment, methods for forming precise windows in an insulator material on a multi-electrode assembly. In another embodiment, a contact assembly for a continuous analyte sensor having more than one working electrode.

18 Claims, 8 Drawing Sheets

(51) Int. Cl.
 *A61B 5/145* (2006.01)
 *C12Q 1/00* (2006.01)

(56) References Cited

U.S. PATENT DOCUMENTS

| | | | | |
|---|---|---|---|---|
| 2009/0131768 | A1* | 5/2009 | Simpson | A61B 5/0031 600/309 |
| 2010/0116691 | A1* | 5/2010 | Papadimitrakopoulos | G01N 33/6803 205/778 |
| 2011/0024307 | A1* | 2/2011 | Simpson | A61B 5/14532 205/782 |
| 2011/0027127 | A1* | 2/2011 | Simpson | A61B 5/14532 422/82.01 |

* cited by examiner

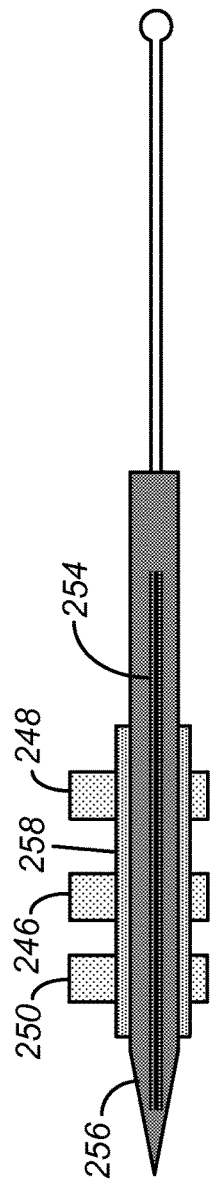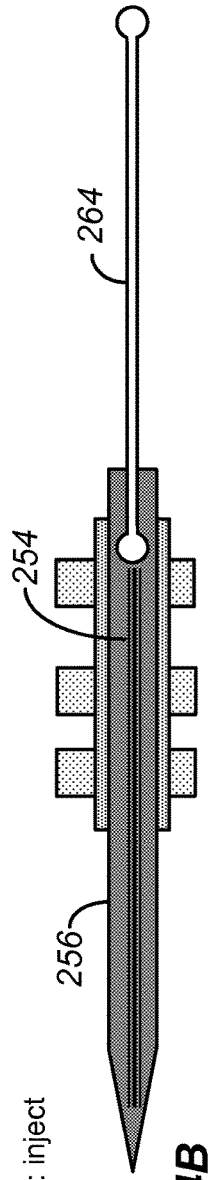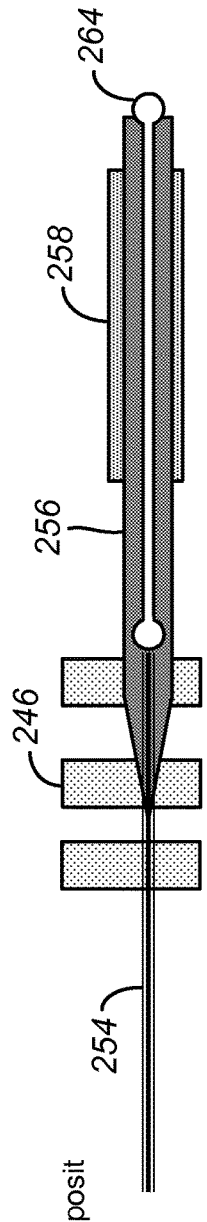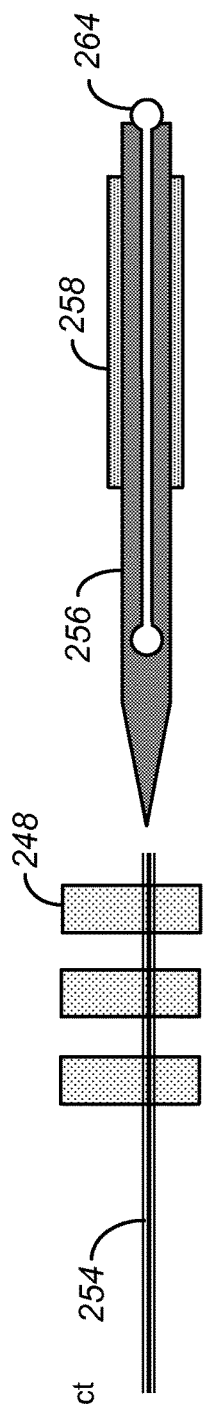
Step 1: start
FIG. 14A
Step 2: inject
FIG. 14B
Step 3: deposit
FIG. 14C
Step 4: retract
FIG. 14D

MULTIPLE ELECTRODE SYSTEM FOR A CONTINUOUS ANALYTE SENSOR, AND RELATED METHODS

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 61/705,066 filed Sep. 24, 2012, the disclosure of which is hereby expressly incorporated by reference in their entirety and is hereby expressly made a portion of this application.

TECHNICAL FIELD

The present embodiments relate to systems and methods for measuring an analyte concentration in a host.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements can be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful information, such as blood glucose expressed in mg/dL.

SUMMARY

The various present embodiments have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One aspect of the present embodiments includes the realization that for sensors that include multiple working electrodes, it may be advantageous for the electrodes to be positioned as closely as possible to one another. Placing the electrodes close together enables both to be affected equally by the analyte, resulting in greater accuracy of signal measurement. However, one problem with placing the electrodes close together is the increased likelihood of crosstalk. Crosstalk describes a phenomenon whereby one or more byproducts of an enzymatic reaction that occurs at a first working electrode migrate to a second working electrode, are sensed by the second working electrode, and are misinterpreted as a greater concentration of analyte than is actually present. Some of the present embodiments provide solutions to this problem.

In recognition of the foregoing problem, certain of the present embodiments, in a first aspect, a continuous analyte sensor is provided, comprising: a first working electrode; a second working electrode; and a membrane overlying at least a portion of the sensor, including the first and second working electrodes, the membrane being continuous, but for a first portion located between the first and second working electrodes that has properties that differ from properties of other portions of the membrane. In an embodiment of the first aspect, at least one of the properties is permeability. In an embodiment of the first aspect, the first portion is cross-linked. In an embodiment of the first aspect, the other portions are cross-linked, and the first portion is cross-linked by an amount different from the other portions. In an embodiment of the first aspect, the first portion has a lower content of a hydrophilic species than the other portions. In an embodiment of the first aspect, the hydrophilic species is removed by a secondary removal process, a leaching process, or a precipitation process involving heat, pH, or solvents. In an embodiment of the first aspect, the first portion comprises a scavenging material, the scavenging material configured to scavenge at least a portion of a byproduct of a chemical reaction occurring at the first working electrode between an analyte and a reactant. In an embodiment of the first aspect, the byproduct comprises hydrogen peroxide. In an embodiment of the first aspect, the scavenging material comprises peroxidase or catalase. In an embodiment of the first aspect, the scavenging material is deposited on the sensor using masking followed by dipping, or by selective spraying. In an embodiment of the first aspect, the first portion comprises an interruption in the membrane properties. In an embodiment of the first aspect, the first portion comprises a mechanical ring that encircles the membrane. In an embodiment of the first aspect, the first working electrode is located on a first wire, the second working electrode is located on a second wire, and the first and second wires are non-concentric.

In a second aspect, a method of producing a continuous analyte sensor, the sensor including a first working electrode, a second working electrode, and a membrane overlying the first and second working electrodes is provided, a method comprising: treating a first portion of the membrane located between the first and second working electrodes, such that the first portion has properties that differ from properties of other portions of the membrane. In an embodiment of the second aspect, at least one of the properties is permeability. In an embodiment of the second aspect, the treating comprises cross-linking. In an embodiment of the second aspect, the method further comprises cross-linking the other portions by an amount different from the first portion. In an embodiment of the second aspect, the treating comprises reducing a content of a hydrophilic species in the first portion. In an embodiment of the second aspect, the hydrophilic species is reduced by a secondary removal process, a leaching process, or a precipitation process involving heat, pH, or solvents. In an embodiment of the second aspect, the treating comprises adding a scavenging material to the first portion, the scavenging material configured to scavenge at least a portion of a byproduct of a chemical reaction occurring at the first working electrode between an analyte and a reactant. In an embodiment of the second aspect, the byproduct comprises hydrogen peroxide. In an embodiment of the second aspect, the scavenging material comprises peroxidase or catalase. In an embodiment of the second aspect, the scavenging material is deposited on the sensor using masking followed by dipping, or by selective spraying. In an embodiment of the second aspect, the treating comprises removing the first portion to create a gap in the membrane. In an embodiment of the second aspect, the treating comprises adding a mechanical ring encircling the first portion.

Another aspect of the present embodiments includes the realization that for sensors that include multiple working electrodes, it is advantageous for membranes covering the electrodes to have thicknesses as close as possible to one another. That is because typically the signal of one of the electrodes is subtracted from the signal of another one of the electrodes to correct for non-analyte or background signal. If the membranes are different thicknesses, the analyte will interact with them differently, making the signal subtraction more challenging. Some of the present embodiments provide solutions to this problem.

In recognition of the foregoing problem, certain of the present embodiments, in a third aspect, a continuous analyte sensor is provided, comprising: a first wire comprising a first working electrode; a second wire comprising a second working electrode; an insulating layer electrically insulating the first wire from the second wire; a conductive layer at least partially surrounding the insulating layer; a first window exposing a first area of the first wire that is electrically connected to the first working electrode and configured to electrically connect with sensor electronics; a second window exposing a second area of the second wire that is electrically connected to the second working electrode and configured to electrically connect with the sensor electronics; and an opening electrically isolating a first portion of the conductive layer adjacent the first area of the first wire from a second portion of the conductive layer adjacent the second area of the second wire. In an embodiment of the third aspect, the first and second windows are created through the conductive layer. In an embodiment of the third aspect, the first and second windows are created through the insulating layer. In an embodiment of the third aspect, the opening is created through the conductive layer. In an embodiment of the third aspect, the opening is created through the insulating layer. In an embodiment of the third aspect, the sensor further comprises a first elastomeric conductive band around the first portion of the conductive layer and contacting the first area of the first wire, and a second elastomeric conductive band around the second portion of the conductive layer and contacting the second area of the second wire. In an embodiment of the third aspect, the elastomeric conductive bands comprise silicone rubber containing carbon particles. In an embodiment of the third aspect, each of the elastomeric conductive bands includes a radially inwardly directed bulge that contacts a respective one of the wires. In an embodiment of the third aspect, the sensor further comprises a conductive paste disposed between at least one of the elastomeric conductive bands and a respective one of the wires. In an embodiment of the third aspect, at least one of the first area of the first wire and the second area of the second wire extends completely around its respective one of the wires. In an embodiment of the third aspect, the first and second working electrodes are located along an in vivo portion of the sensor, and the first and second windows are located along an ex vivo portion of the sensor.

In a fourth aspect, a method of making a continuous analyte sensor is provided, a method comprising: coating a first conductive wire and a second conductive wire with an insulating layer, thereby electrically insulating the first and second wires from one another; coating the insulating layer with a conductive layer; removing first and second spaced bands of the conductive layer and the insulating layer to create first and second sections of the conductive layer and the insulating layer that are spaced and electrically isolated from one another; and removing first and second windows from the first and second sections to expose first and second areas of the first and second wires, respectively. In an embodiment of the fourth aspect, the method further comprises disposing first and second elastomeric conductive bands about the first and second sections to contact the first and second areas, respectively. In an embodiment of the fourth aspect, the elastomeric conductive bands comprise silicone rubber containing carbon particles. In an embodiment of the fourth aspect, each of the elastomeric conductive bands includes a radially inwardly directed bulge that contacts a respective one of the wires. In an embodiment of the fourth aspect, the method further comprises disposing a conductive paste between at least one of the elastomeric conductive bands and a respective one of the wires. In an embodiment of the fourth aspect, at least one of the first area of the first wire and the second area of the second wire extends completely around its respective one of the wires.

Another aspect of the present embodiments includes the realization that for multi-wire sensors it can be challenging to electrically connect the electrodes with sensor electronics while maintaining a low profile for the sensor. It is advantageous if a sensor is capable of being inserted through the skin using an ordinary needle, rather than one with a channel or other structure that makes the needle more expensive and the overall structure more complicated.

In recognition of the foregoing problem, certain of the present embodiments, in a fifth aspect, a continuous analyte sensor is provided, comprising: a first wire comprising a first working electrode; a second wire comprising a second working electrode; and a membrane system overlying the electrodes, wherein the membrane system has different enzymatic properties in a first area overlying the first working electrode than in a second area overlying the second working electrode, but substantially equal thickness and substantially equal permeability in the first and second areas. In an embodiment of the fifth aspect, the thickness of the membrane system in the first area is within one micron of the thickness of the membrane system in the second area. In an embodiment of the fifth aspect, the permeability of the membrane system in the first area is within 5% of the permeability of the membrane system in the second area. In an embodiment of the fifth aspect, the sensor further comprises an insulating layer electrically isolating the first wire from the second wire.

In a sixth aspect, a continuous analyte sensor is provided, comprising: a first wire comprising a first working electrode; a second wire comprising a second working electrode; a first membrane overlying the first working electrode; and a second membrane overlying both the first working electrode and the second working electrode; wherein a thickness of the second membrane overlying the second working electrode is not substantially equal to a combined thickness of the first and second membranes overlying the first working electrode; and wherein the second membrane overlying the second working electrode and the combined first and second membranes overlying the first working electrode have substantially the same permeability to an analyte. In an embodiment of the sixth aspect, the thickness of the second membrane overlying the second working electrode is within one micron of the combined thickness of the first and second membranes overlying the first working electrode. In an embodiment of the sixth aspect, the permeability of the second membrane overlying the second working electrode is within 5% of the permeability of the combined first and second membranes overlying the first working electrode. In an embodiment of the sixth aspect, the sensor further comprises an insulating layer electrically isolating the first wire from the second wire.

In a seventh aspect, a method of making a continuous analyte sensor comprising a first working electrode and a second working electrode is provided, the method comprising: dipping the sensor in a first solution until an exposed electroactive area of the first working electrode is submerged, and withdrawing the sensor from the first solution, thereby forming a first membrane on the first working electrode; and dipping the sensor in a second solution until the exposed electroactive area of the first working electrode is submerged and an exposed electroactive area of the second working electrode is submerged, and withdrawing the sensor from the second solution, thereby forming a second membrane on both the first working electrode and the second working electrode; wherein withdrawing the sensor from the second solution comprises withdrawing at a first withdrawal rate until the exposed electroactive area of the second working electrode is no longer submerged, and then withdrawing at a second withdrawal rate until the exposed electroactive area of the first working electrode is no longer submerged. In an embodiment of the seventh aspect, the second withdrawal rate is faster than the first withdrawal rate. In an embodiment of the seventh aspect, the method further comprises, prior to dipping the sensor in the first and second solutions, dipping the sensor in another solution that provides the sensor with a function of at least one of resistance, blocking, interference, and electrolyte.

In an eighth aspect, a continuous analyte sensor, wherein the sensor is formed is provided, comprising: dipping the sensor in a first solution until an exposed electroactive area of the first working electrode is submerged, and withdrawing the sensor from the first solution, thereby forming a first membrane on the first working electrode; and dipping the sensor in a second solution until the exposed electroactive area of the first working electrode is submerged and an exposed electroactive area of the second working electrode is submerged, and withdrawing the sensor from the second solution, thereby forming a second membrane on both the first working electrode and the second working electrode; whereby a membrane system is formed having different enzymatic properties in a first area overlying the exposed electroactive area of the first working electrode than in a second area overlying the exposed electroactive area of the second working electrode, but substantially equal thickness and substantially equal permeability in the first and second areas.

Another aspect of the present embodiments includes the realization that one challenge with multi-electrode sensor systems includes forming precise "windows" within an insulator material that surrounds the conductive wires. For example, it can be difficult to remove insulator from (or not deposit insulator on) specific portions of the wire(s) to expose electroactive surfaces for sensing. Some of the present embodiments provide solutions to this problem.

Another aspect of the present embodiments includes the realization that one challenge with multi-electrode sensor systems includes assembling multiple wires with a base structure. It would be advantageous to reduce manual alignment steps during assembly with a base.

BRIEF DESCRIPTION OF THE DRAWINGS

The various present embodiments now will be discussed in detail with an emphasis on highlighting the advantageous features. These embodiments depict the novel and non-obvious multiple electrode system for a continuous analyte sensor, and related methods, shown in the accompanying drawings, which are for illustrative purposes only. These drawings include the following figures, in which like numerals indicate like parts:

FIGS. 14A-14D are schematic side cross-sectional views illustrating a process for inserting a sensor;

DETAILED DESCRIPTION

Figure 1:
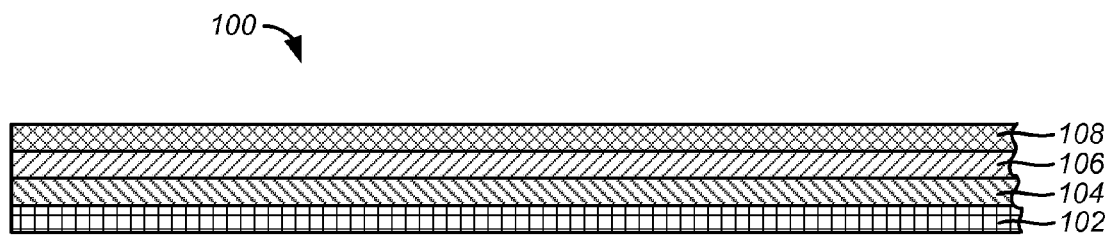
FIG. 1 is a schematic side cross-sectional view of a layered membrane system configured for use with the present embodiments.

The following detailed description describes the present embodiments with reference to the drawings. In the drawings, reference numbers label elements of the present embodiments. These reference numbers are reproduced below in connection with the discussion of the corresponding drawing features.

The present embodiments are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

Generally, implantable sensors measure a signal (e.g., counts) related to an analyte of interest in a host. For example, an electrochemical sensor can measure glucose, creatinine, or urea in a host, such as an animal, especially a human. Generally, the signal is converted mathematically to a numeric value indicative of analyte status, such as analyte concentration.

The preferred embodiments provide a continuous analyte sensor that measures a concentration of the analyte of interest or a substance indicative of the concentration or presence of the analyte. In some embodiments, the analyte sensor is an invasive, minimally invasive, or non-invasive device, for example a subcutaneous, transdermal, or intravascular device. In some embodiments, the analyte sensor may analyze a plurality of intermittent biological samples. The analyte sensor may use any method of analyte-measurement, including enzymatic, chemical, physical, electrochemical, spectrophotometric, polarimetric, calorimetric, radiometric, etc.

In general, analyte sensors provide at least one working electrode and at least one reference electrode, which are configured to measure a signal associated with a concentration of the analyte in the host. In general, continuous analyte sensors define a relationship between sensor-generated measurements (for example, current in nA or digital counts after A/D conversion) and a reference measurement (for example, mg/dL or mmol/L) that are meaningful to a user. The output signal is typically a raw data stream that is used to provide a useful value of the measured analyte concentration in a host to the patient or doctor, for example. However, the analyte sensors of the preferred embodiments may comprise at least one additional working electrode configured to measure at least one additional signal, as discussed elsewhere herein.

Preferred Sensor Components

In general, sensors of the preferred embodiments describe a variety of sensor configurations, wherein each sensor generally comprises two or more working electrodes, a reference and/or counter electrode, an insulator, and a membrane system configured to substantially reduce and/or eliminate noise and/or interferents. In general, the sensors can be configured to continuously measure an analyte in a biological sample, for example, in subcutaneous tissue, in a host's blood flow, etc. Although a variety of example embodiments are shown, one skilled in the art appreciates that the concepts and examples here can be combined, reduced, substituted, or otherwise modified in accordance with the teachings of the preferred embodiments and/or the knowledge of one skilled in the art.

Some embodiments are configured to measure the current flow and/or current density (i.e., sensitivity divided by surface area of the electroactive surface) in the picoAmp range, and in some embodiments, femtoAmps. In some embodiments, the first sensitivity is from about 20 pA/mg/dL to about 300 pA/mg/dL, or from about 50 pA/mg/dL to about 100 pA/mg/dL. In some of these embodiments, the current density is from about 65 pA/mg/dL/mm$^2$ to about 1,000 pA/mg/dL/mm$^2$, or from about 165 pA/mg/dL/mm$^2$ to about 1,700 pA/mg/dL/mm$^2$.

Preferably, each example sensor design includes first and second working electrodes. In some embodiments, the sensor is configured with an architecture smaller than about 1 mm in at least one dimension. For example, in some embodiments, each electrode is formed from a fine wire with a diameter of from about 0.001 or less to about 0.01 inches or more, for example, and is formed from, e.g. a plated insulator, a plated wire, or bulk electrically conductive material. In preferred embodiments, the working electrodes comprise wires formed from a conductive material, such as platinum, platinum-iridium, palladium, graphite, gold, carbon, conductive polymer, alloys, etc. Although the electrodes can by formed by a variety of manufacturing techniques (bulk metal processing, deposition of metal onto a substrate, etc.), it can be advantageous to form the electrodes from plated wire (e.g., platinum on steel wire) or bulk metal (e.g., platinum wire). In embodiments wherein the sensor is formed from an elongated core (e.g., wire), the core can be formed of any of a variety of suitable material, such as, platinum, platinum-iridium, gold, palladium, iridium, graphite, carbon, conductive or non-conductive polymer, alloys, glass, for example. In some embodiments, the elongated core (e.g., wire) comprises an inner core and a first layer, wherein an exposed electroactive surface of the first layer provides the working electrode of the continuous analyte sensor being manufactured. For example, in some embodiments, the inner core comprises stainless steel, titanium, tantalum and/or a polymer, and the first layer comprises platinum, platinum-iridium, gold, palladium, iridium, graphite, carbon, a conductive polymer, and/or an alloy. In some embodiments of the multifilar sensor, the two or more electrode cores (e.g., wires) are embedded within, coated with, extruded together and/or otherwise formed with insulating attachment. While in some embodiments described herein, the sensor is formed from a wire with a circular cross-section, in other embodiments the cross-section of the sensor (or elongate core that forms each electrode) can be oval, square, rectangular, triangular, polyhedral, star-shaped, C-shaped, T-shaped, X-shaped, Y-Shaped, irregular, or the like.

Preferably, the first working electrode is configured to measure the concentration of an analyte. In an enzymatic electrochemical sensor for detecting glucose, for example, the first working electrode measures the hydrogen peroxide produced by an enzyme catalyzed reaction of the analyte being detected and creates a measurable electric current. For example, in the detection of glucose wherein glucose oxidase (GOX) produces hydrogen peroxide as a byproduct, hydrogen peroxide ($H_2O_2$) reacts with the surface of the working electrode producing two protons ($2H^+$), two electrons (2e⁻) and one molecule of oxygen ($O_2$), which produces the electric current being detected.

Preferably, each example sensor design includes at least one additional working electrode configured to measure a non-analyte-related signal (e.g., baseline, background, etc.), to measure another analyte (e.g., oxygen), to generate oxygen, and/or as a transport-measuring electrode, all of which are described in more detail elsewhere herein. In general, the additional working electrode(s) can be formed as described with reference to the first working electrode. In one embodiment, the auxiliary (additional) working electrode is configured to measure a background signal, including constant and non-constant analyte signal components.

Preferably, each example sensor design includes a reference and/or counter electrode. In general, the reference electrode has a configuration similar to that described elsewhere herein with reference to the first working electrode. The reference electrode may be formed from materials such as silver, silver/silver chloride, calomel, Copper-copper(II) sulfate, etc. In some embodiments, the reference electrode is integrally formed with the one or more working electrodes, however other configurations are also possible (e.g. remotely located on the host's skin, or otherwise in bodily fluid contact). In some alternative embodiments, the reference electrode is disposed remotely from the sensor, such as but not limited to on the host's skin, as described herein.

Preferably, each example sensor design includes an insulator (e.g., non-conductive material) or similarly functional component. In some embodiments, one or more electrodes are covered with an insulating material, for example, a non-conductive polymer. Dip-coating, spray-coating, vapor-deposition, or other coating or deposition techniques can be used to deposit the insulating material on the electrode(s). In some embodiments, the insulator is a separate component of the system and can be formed as is appreciated by one skilled in the art. Any suitable insulating material can be used, for example, fluorinated polymers, polyethyleneterephthalate, polyurethane, polyimide, parylene, other non-conducting polymers, etc. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa.

Preferably, each example sensor design includes exposed electroactive area(s). In embodiments wherein an insulator is disposed over one or more electrodes, a portion of the coated electrode(s) can be stripped or otherwise removed, for example, by hand, excimer lasing, chemical etching, laser ablation, laser skiving, grit-blasting (e.g. with sodium bicarbonate or other suitable grit), etc., to expose the electroactive surfaces. Alternatively, a portion of the electrode can be masked prior to depositing the insulator in order to maintain an exposed electroactive surface area. ""In some embodiments, the tip (e.g., end) of the sensor is cut to expose electroactive surface areas, without a need for removing insulator material from sides of insulated electrodes. In general, a variety of surfaces and surface areas can be exposed.

One challenge with multi-electrode sensor systems includes forming precise "windows" within an insulator material that surrounds the conductive wires. For example, it can be difficult to remove insulator from (or not deposit insulator on) specific portions of the wire(s) to expose electroactive surfaces for sensing. The present embodiments provide systems and methods for removing portions of insulator material from a multi-electrode assembly, and for depositing insulator material on a multi-electrode assembly, precisely and with ease of manufacture.

In one embodiment, two or more different insulator materials are used to coat the electrode materials, wherein the materials have different properties with regard to their ability to be removed with a laser. For example, polyimide is a first insulator material that requires a first type of laser to ablate the material, whereas parylene is a second insulator material that requires a second (different) type of laser to ablate the material (e.g., different wavelengths).

In another embodiment, an insulator material is modified by one or more UV absorber additives. In this embodiment, selective ablation of the insulator material can be provided by selecting the wavelength of the laser(s) used to remove the insulator material.

In another embodiment, the insulator can be selected such that an organic solvent applied to the surface of the insulator precisely removes a portion thereof. In one embodiment, the concentration of the solvent is modulated to provide more working time, after which a non-solvent can be used to stop the dissolution.

In another embodiment, such as photolithography or photoengraving, a photoresist uses a light-sensitive material to form a patterned coating on the portion of the surface of the insulator where the exposed electroactive windows are to be cut. Both positive and negative photoresist methods are possible. A positive resist is a type of photoresist in which the portion of the photoresist that is exposed to light becomes soluble to the photoresist developer and the portion of the photoresist that is unexposed remains insoluble to the photoresist developer. A negative resist is a type of photoresist in which the portion of the photoresist that is exposed to light becomes relatively insoluble to the photoresist developer. The unexposed portion of the photoresist is dissolved by the photoresist developer.

In another embodiment, a ripcord is co-extruded into the sensor assembly, for example beneath the insulator material, leaving a tag of the ripcord exposed above the insulator. The ripcord is then "ripped" to expose the desired electroactive working window.

In another embodiment, the insulator is selectively deposited over a mask configured to inhibit deposition of the insulator on the desired electroactive window(s).

In another embodiment, a rotary grinder, such as a Dremel tool, precisely grinds away the insulator at the desired location of the window(s).

Preferably, each example sensor design includes a membrane system. Preferably, a membrane system is deposited over at least a portion of the electroactive surfaces of the sensor (working electrode(s) and optionally reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface. Some examples of suitable membrane systems are described in U.S. Patent Application Publication No. 2005/0245799.

With reference to FIG. 1, in general the membrane system 100 includes a plurality of domains (or layers), for example, one or more of an electrode domain 102, an interference domain 104, an enzyme domain 106 (for example, including glucose oxidase), and a resistance domain 108. The membrane system 100 may also include a high oxygen solubility domain, and/or a bioprotective domain (not shown), such as is described in more detail in U.S. Patent Application Publication No. 2005/0245799. While the embodiment illustrated in FIG. 1 shows the interference domain 104 between the electrode domain 102 and the enzyme domain 106, the interference domain 104 can be disposed more proximal or more distal to the electroactive surfaces. For example, in some embodiments, the interference domain 104 is more distal to the electroactive surfaces than the enzyme domain 106. In some embodiments, the interference domain 104 is the most distal layer/domain of the membrane system 100, relative to the electroactive surfaces. In some embodiments, the interference domain 104 can be the most proximal domain/layer, relative to the electroactive surfaces. In still other embodiments, the interference domain 104 can be combined with one or more other membrane domains/ layers. For example, in some embodiments, the interference domain 104 and the resistance domain 108 are combined into a single domain that provides both interference blocking and control of analyte flux. In some embodiments, the membrane system 100 includes one or more domains not illustrated in FIG. 1, such as but not limited to a bioprotective domain (e.g., cell disruptive domain), etc. A wide variety of configurations and combinations for the various layers in the membrane system are encompassed by the preferred embodiments. In various embodiments, any of the domains illustrated in FIG. 1 may be omitted, altered, substituted for, and/or incorporated together without departing from the spirit of the preferred embodiments The membrane system can be deposited on the exposed electroactive surfaces using known thin film techniques (for example, vapor deposition, spraying, electro-depositing, dipping, etc.). In alternative embodiments, however, other vapor deposition processes (e.g., physical and/or chemical vapor deposition processes) can be useful for providing one or more of the insulating and/or membrane layers, including ultrasonic vapor deposition, electrostatic deposition, evaporative deposition, deposition by sputtering, pulsed laser deposition, high velocity oxygen fuel deposition, thermal evaporator deposition, electron beam evaporator deposition, deposition by reactive sputtering molecular beam epitaxy, atmospheric pressure chemical vapor deposition (CVD), atomic layer CVD, hot wire CVD, low-pressure CVD, microwave plasma-assisted CVD, plasma-enhanced CVD, rapid thermal CVD, remote plasma-enhanced CVD, and ultra-high vacuum CVD, for example. However, the membrane system can be disposed over (or deposited on) the electroactive surfaces using any known method, as will be appreciated by one skilled in the art. In general, each domain or layer is formed by applying a coating solution (e.g., electrode solution, interference solution, enzyme solution (or non-enzyme solution), resistance solution, and the like. Each solution comprises a coating solution formed of a solvent and a coating material; the coating material may include polymers, suspensions, binders, and the like, as appreciated by one skilled in the art. With regard to the enzyme solution and no-enzyme solution, it is meant that the non-enzyme solution contains the same composition of materials as the enzyme solution, except the enzyme component. For example, wherein the enzyme layer is formed from a polyurethane, for example, aqueous dispersions of colloidal polyurethane polymers including the enzyme; the non-enzyme layer is formed from the same polyurethane, but not including the enzyme.

Bifilar Sensor

One embodiment of a dual electrode sensor system includes a first working electrode configured to generate a first signal associated with glucose and non-glucose related electroactive compounds, and a second working electrode configured to generate a second signal associated with noise of the glucose sensor. The noise comprises signal contribution due to non-glucose related electroactive compounds. In some designs, the sensor further includes one or more reference electrodes and/or counter electrodes. Also in some designs, the first and second working electrodes and the reference electrode each integrally form a substantial portion of the sensor configured for insertion in the host. For example the wires or electrode materials may be twisted together, bonded together (e.g., via an insulator material), extruded together, formed as a unit, etc.

Figure 2:
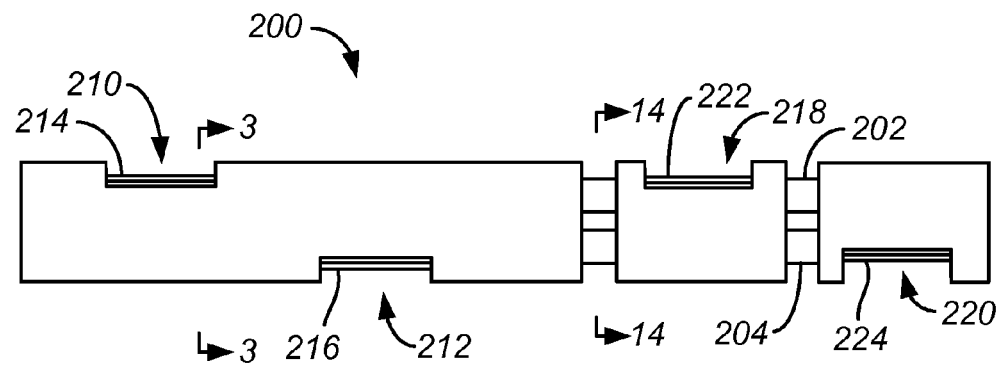
FIG. 2 is a schematic side elevation view of one of the present embodiments of a continuous analyte sensor.

FIG. 2 illustrates an example of a continuous analyte sensor 200 configured to continuously measure analyte concentration (e.g., glucose concentration) in a host to provide a data stream representative of the host's analyte concentration, in accordance with the present embodiments. The sensor 200 comprises a first electrically conductive wire 202 and a second electrically conductive wire 204. Preferred materials for the wires 202, 204 are described above, and will not be repeated here. The wires 202, 204 extend in a parallel, non-concentric arrangement. In other embodiments, the wires 202, 204 may be arranged differently, such as concentrically. The arrangement of the wires 202, 204 is not germane to the scope of the present disclosure, and could comprise any arrangement. Because the sensor 200 comprises two wires 202, 204, it may be referred to as a bifilar sensor 200. However, in other embodiments the sensor 200 may have more than two wires, such as three (trifilar) or more wires.

Figure 3:
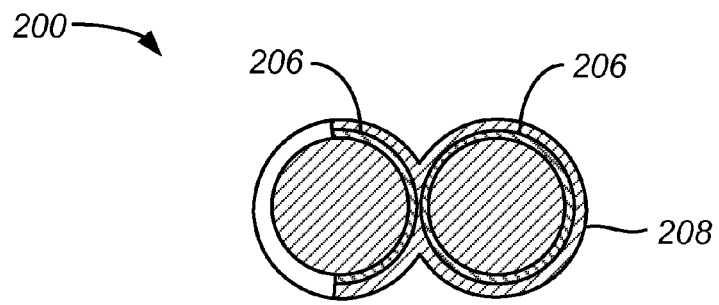
FIG. 3 is a schematic cross-sectional view of the sensor of FIG. 2 taken along the line 3-3.

With reference to the cross-sectional view FIG. 3, each of the wires 202, 204 includes an insulative coating 206. Preferred materials for the insulator 206 are described above, and will not be repeated here. The insulator 206 completely surrounds each wire 202, 204, except in limited areas that are described in further detail below. The insulator 206 thus electrically isolates the wires 202, 204 from one another. An outer conductive layer 208 surrounds the insulator 206. Like the insulator 206, the outer conductive layer 208 completely surrounds each wire 202, 204, except in limited areas that are described in further detail below. The outer conductive layer 208 also secures the two wires 202, 204 to one another. Preferred materials for the outer conductive layer 208 include silver containing (e.g., Ag/AgCl), calomel containing, Copper-copper(II) sulfate containing, or the like. The conductive-containing material may include any of a variety of materials and be in various forms, such as, Ag/AgCl-polymer pastes, paints, polymer-based conducting mixture, and/or inks that are commercially available, for example and may be processed using a pasting/ dipping/coating step, for example. In certain embodiments, the outer conductive layer 208 may not extend the entire length of the sensor 200, and may instead be located in only selected discrete locations.

With reference to FIG. 2, portions of the insulator 206 and outer conductive layer 208 are removed from the sensor 200 to expose the conductive wires 202, 204. Processes for removing these portions are described above, and will not be repeated here. To the left-hand side of FIG. 2, and with reference to the cross-sectional view FIG. 3, the material covering approximately half of the diameter of each wire 202, 204 is removed to create first and second windows 210, 212. As discussed further below, the portions of the wires 202, 204 in the areas of the first and second windows 210, 212 each comprise working electrodes 214, 216. To the right-hand side of FIG. 2, the material covering approximately half of the diameter of each wire 202, 204 is removed to create third and fourth windows 218, 220. As discussed further below, the portions of the wires 202, 204 in the areas of the third and fourth windows 218, 220 each comprise contacts 222, 224. On either side of the third window 218, the material covering the each wire 202, 204 (in part or in whole, for example leaving bare wire with spacing to electrically isolate wires 202 and 204 and/or insulation around or between wires 202, 204) is removed so that the contacts 222, 224 are electrically isolated from one another and from the working electrodes 214, 216.

Figure 5:
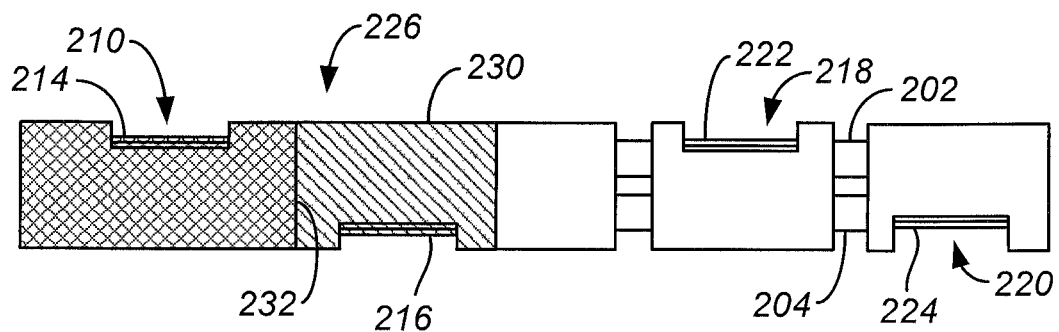
FIG. 5 is a schematic side elevation view of another of the present embodiments of a continuous analyte sensor.

The working electrodes 214, 216 are at least partially covered with a membrane 226 (FIG. 5). Portions of the membrane 226 overlying the working electrodes 214, 216 may include one or more additives, such as an enzyme, that react chemically with an analyte of interest. For example, one of the working electrodes 214, 216 may include an enzyme while the other working electrode does not include an enzyme. In other examples, both of the working electrodes 214, 216 may include an enzyme, where the enzymes over each of the working electrodes 214, 216 are different. Examples of combinations for membrane 226 additives include: Glucose oxidase (GOX)-Glutamate dehydrogenase (GDH) enzymes, GOX-lactate, GDH-lactate, lactate-ketone, GOX-ketone, GDH-ketone, GOX-free fatty acids (2 enzyme systems), GDH-free fatty acids, lactate-free fatty acids, lactate-cholesterol, cholesterol-free fatty acids, lactate-cardiac markers, creatine-lactate, creatine-cardiac markers, and other combinations. In each of the foregoing combinations, the membrane 226 has different enzymatic properties over each of the electrodes. It should be understood that "different enzymatic properties" encompasses a combination where one of the electrodes includes no enzyme. Further, where the membrane 226 includes multiple layers, including an enzyme layer 228, the enzyme layer 228 may or may not comprise enzyme.

Figure 4:
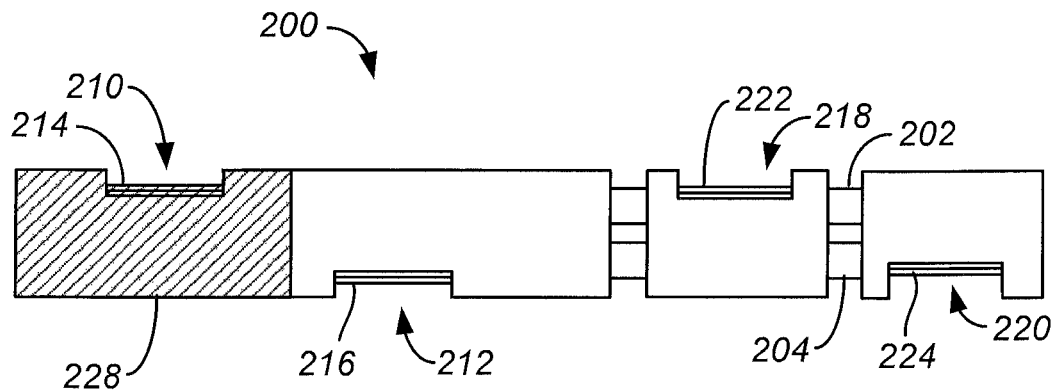
FIG. 4 is a schematic side elevation view of another of the present embodiments of a continuous analyte sensor.

Referring to FIG. 2, and as discussed in further detail below, in one embodiment of a method of manufacturing the sensor 200, the sensor 200 is dipped in an enzyme solution up to a point between the first and second windows 210, 212. This step coats the first working electrode with an enzyme solution to form an enzyme layer 228 (FIG. 4). Following the enzyme dip, the sensor 200 is dipped in a non-enzyme solution up to a point where both windows 210, 212 are submerged to form a non-enzyme layer. This step coats both working electrodes 214, 216 with a non-enzyme layer 230 (FIG. 5), with the portion of the non-enzyme layer 230 overlying the first working electrode 214 also overlying the enzyme layer 228. Finally, the sensor 200 may be dipped almost up to the contacts 222, 224 in a resistance layer solution (not shown).

Under some conditions, crosstalk may develop between the enzyme electrode 214 (WE) and the non-enzyme electrode 216 (NE). Crosstalk shows up as a glucose depending signal at the NE electrode 216. It is believed that this crosstalk is due to diffusion of a measurable species (e.g., hydrogen peroxide in a conventional glucose oxidase electrode) generated by glucose conversion in the enzyme layer 228 of the WE electrode 214. This peroxide then travels by diffusion under the resistance layer to the NE electrode 216. Some of the present embodiments provide solutions to this problem.

With reference to FIG. 5, in one embodiment crosstalk can be reduced by increasing the distance between the end 232 of the enzyme layer 228 and the NE electrode 216, thereby increasing the distance to be overcome by diffusion and reducing the magnitude of crosstalk. In one example embodiment, the distance can be increased by dipping in enzyme solution only up to an edge of the WE 214 nearest the NE 216, so that little to no enzyme solution extends past the WE 214 in the direction of the NE 216. In an alternative embodiment, the physical distance between WE 214 and NE 216 can be increased. For example, the physical distance between WE 214 and NE 216 may be about 0.025, 0.020, 0.015, 0.01 or 0.005 inches.

Figure 6:
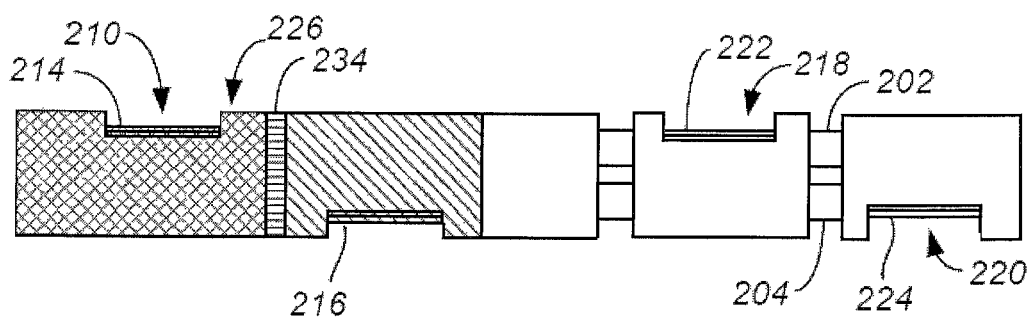
FIG. 6 is a schematic side elevation view of another of the present embodiments of a continuous analyte sensor.

With reference to FIG. 6, in another embodiment crosstalk can be reduced by altering, modulating and/or tuning the permeability properties of the membrane 226 in the area between the WE 214 and the NE 216. For example, the permeability properties of the membrane 226 could be tuned in a band 234 encircling the sensor 200 between the WE 214 and the NE 216, as shown in FIG. 6. One example of a technique for tuning the permeability properties of the membrane 226 is cross-linking. Cross-links are bonds that link one polymer chain to another to promote a difference in the polymers' physical properties. In these embodiments, the change in the polymers' physical properties could comprise a reduction in the permeability of the membrane 226 in the cross-linked band 234. A reduction in permeability would cause any hydrogen peroxide in the membrane 226 to alter its flux upon reaching the cross-linked band 234, rather than migrating to the NE 216, because the peroxide molecules will follow the path of least resistance. Since less hydrogen peroxide (or no hydrogen peroxide) would reach the NE 216, the magnitude of crosstalk would be reduced.

In general, crosslinking refers to joining (e.g., adjacent chains of a polymer or protein) by creating covalent bonds. Crosslinking can be accomplished by techniques such as thermal reaction, chemical reaction or by providing ionizing radiation (for example, electron beam radiation, UV radiation, or gamma radiation). In some embodiments, the first portion is crosslinked by forming free radicals, which may include the use of ionizing radiation (e.g., gamma radiation), thermal initiators, chemical initiators, photoinitiators (e.g., UV and visible light), and the like. Any suitable initiator or any suitable initiator system can be employed, for example, α-hydroxyketone, α-aminoketone, ammonium persulfate (APS), redox systems such as APS/bisulfite, or potassium permanganate. Suitable thermal initiators include but are not limited to potassium persulfate, ammonium persulfate, sodium persulfate, and mixtures thereof. One example technique for cross-linking the membrane 226 comprises irradiating it with light in the presence of monomers and a photoinitiator. By varying the wavelength and/or intensity of the light, properties of the membrane 226 can be tuned to achieve, for example, a desired permeability. Some ethyleneically unsaturated monomers of use include but are not limited to polyethyleneglycol dimethacrylate, N,N'-methylenebismethacrylamide, 1,3-bis(3-methacryloxypropyl)tetramethyldisiloxane, ethylene glycol dimethacrylate, 1,3-bis (3-methacryloxy-2-hydroxypropoxypropyl) tetramethyldisiloxane, methacrylic acid, hydroxyethyl acrylate, N,N-dimethyl acrylamide, triacrylate, 1,3-diallyltetrakis(trimethylsiloxy)disiloxane, (3-acryloxypropyl)tris (trimethylsiloxy)silane, 2-hydroxyethyl methacrylate, methacryloxypropyltris(vinyldimethylsiloxy)silane, acrylamide, trimethyolpropane N,N'-methylenebisacrylamide, methacryloxymethylphenethyltris(trimethylsiloxy)silane, 3-acrylamidopropyltris(trimethylsiloxy)silane, N-vinyl pyrrolidone, and 1,3-bis(3-methacryloxypropyl)tetrakis (trimethylsiloxy)disiloxane. Photoinitiators include those available from Ciba (now part of BASF chemical company) and include the Irgacure and Darocure series, for example Irgacure 2959 and Darocure 1173. Another example technique for cross-linking the membrane involves thermal-initiated free radical polymerization. Thermal polymerization involves the use of an azo initiator such as azobisisobutyronitrile or 2,2'-Azobis[2-(2-imidazolin-2-yl) propane]dihydrochloride in combination with the monomers listed above. Another example technique for cross-linking the membrane involves carbodiimide coupling. Herein a carboxyl or amine functionalized membrane (polyurethane) is reacted with a polycarbodiimide such as Zoldine available from Dow Chemical Company, to afford a crosslinked polymer.

With continued reference to FIG. 6, in another embodiment crosstalk can be reduced by scavenging peroxide diffusing from the WE 214 to the NE 216. For example, a ring 234 of material containing a hydrogen peroxide scavenging agent can be applied in the area between the WE 214 and the NE 216. The scavenging agent reacts with any hydrogen peroxide migrating from the WE 214 to the NE 216, producing one or more reaction products having properties that do not affect the signal produced by the NE 216. In general, a scavenging agent may be any material or polymer capable of oxidizing by reaction with hydrogen peroxide (e.g., certain ring structures in polymers) or providing catalysis of the spontaneous decomposition (e.g., transition metal catalysts silver, platinum, manganese dioxide, iron, titanium) of hydrogen peroxide, and this may include polymers that change the pH (e.g., alkaline pH speeds decomposition).

Some example scavenging agents include, but are not limited to, peroxidase, catalase, or the like. The scavenging agent may be formed, for example, by masking followed by dipping, or by selective spraying, or by any other process. In an alternative embodiment, a peroxide scavenging material can be added to the NE dip solution. This embodiment results in a peroxide scavenging layer on top of the enzyme at the WE electrode 214, which scavenges a fraction of the peroxide generated at the WE electrode 214. As a result, the sensitivity of the sensor 200 is reduced, but crosstalk is attenuated.

Figure 7:
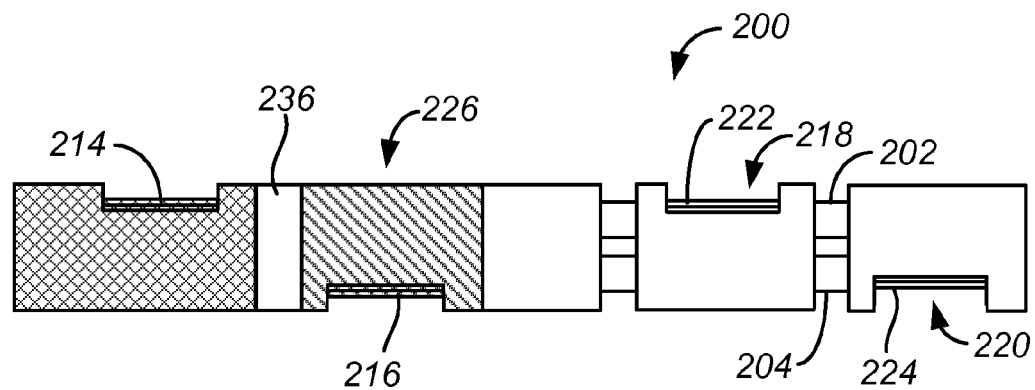
FIG. 7 is a schematic side elevation view of another of the present embodiments of a continuous analyte sensor.

With reference to FIG. 7, in another embodiment crosstalk can be reduced by interrupting the diffusion path between the WE 214 and the NE 216. For example, a small ring of resistance layer and underlying layers may be removed to form an interruption 236 (e.g., an open channel for outward diffusion of the measurable species) in the membrane 226. In certain embodiments, this area of the sensor 200 may also include the conductive layer 208, in which case it may be removed as well, and in still further embodiments the insulator 206 may be removed. Any species (e.g., measurable cross talk species such as peroxide) approaching this interruption 236 will diffuse outward instead of diffusing to the NE electrode 216, because the peroxide molecules will follow the path of least resistance. In other embodiments, to prevent out-diffusion of peroxide (e.g. for biocompatibility reasons), after creating the interruption 236, the sensor 200 may undergo another dip in resistance layer. This dip closes the outward leak and forms a hermetic barrier for diffusing peroxide.

Figure 8:
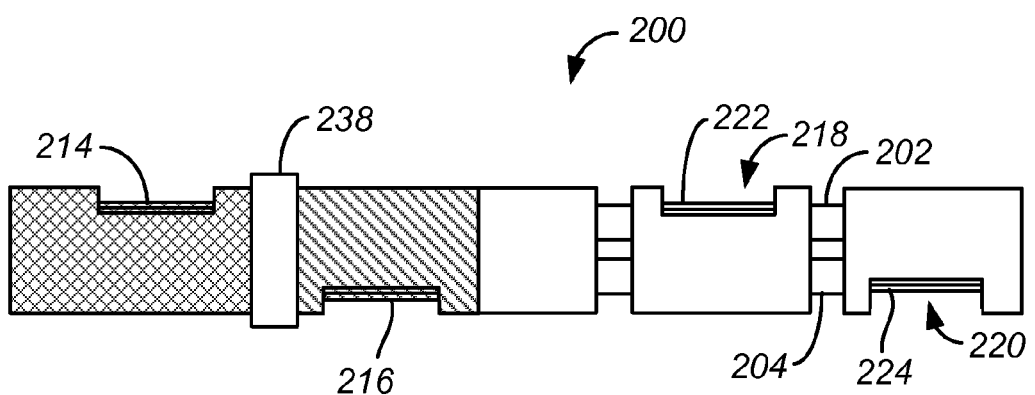
FIG. 8 is a schematic side elevation view of another of the present embodiments of a continuous analyte sensor.

In another example of interrupting the diffusion path between the WE 214 and the NE 216, rather than removing layers, a mechanical ring 238 can be disposed between the WE 214 and the NE 216 to encircle the sensor 200, as shown in FIG. 8. The ring may be formed from any material suitable for in vivo applications and is formed in such a way that the permeability within the membrane is disrupted.

Advantageously, the foregoing embodiments reduce crosstalk by impeding the diffusion of hydrogen peroxide (or other product(s) of chemical reaction(s) at the WE 214) from the WE 214 to the NE 216. The hydrogen peroxide thus does not interfere with the ability of the NE 216 to detect analyte. The precision of the sensor 200 is thus improved.

Another aspect of the present embodiments includes the realization that for sensors that include multiple working electrodes, it is advantageous for membranes covering the electrodes to have thicknesses as close as possible to one another. That is because typically the signal of one of the electrodes is subtracted from the signal of another one of the electrodes to correct for non-analyte or background signal. If the membranes are different thicknesses, the analyte will interact with them differently. For example, a thicker membrane may resist the flux of the analyte of interest or other measureable species. These differences in how the analyte interacts with the membranes make the signal subtraction more challenging. Some of the present embodiments provide solutions to this problem.

In a dipping process for forming a membrane on a sensor, the thickness of the membrane is influenced by at least the following three factors: the rate at which the sensor is withdrawn from the membrane solution, the viscosity of the membrane solution, and the length of the sensor that is submerged in the membrane solution (referred to as surface contact). In the present embodiments, these factors may fall within the following ranges, for example:

Viscosity—from about 50 centipoises to about 400 centipoises, such as from about 80 centipoises to about 300 centipoises, or from about 110 centipoises to about 200 centipoises, or about 135 centipoises;

Withdrawal Rate—from about 2 in/min to about 25 in/min, such as from about 6 in/min to about 20 in/min, from about 10 in/min to about 15 in/min, or about 12 in/min; and Surface Contact—about 0.5 in for a first dip cycle, followed by multiple dip cycles at about 0.2 in.

In some embodiments of a bifilar sensor 200, enzyme solution is applied selectively to the WE 214 and not to the NE 216. A non-enzyme solution is then applied to both the WE 214 and the NE 216. Thus, the membrane system over the WE 214 has at least one more layer than the membrane 226 system over the NE 216. The different number of layers presents a challenge to the goal of having the membrane system be of equal thickness over both the WE 214 and the NE 216.

Figure 9:
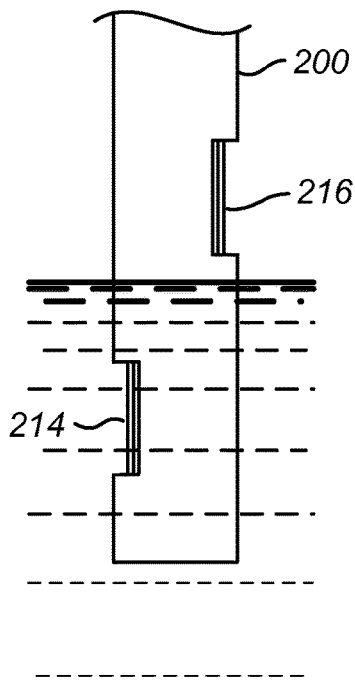
FIGS. 9 and 10 are schematic side elevation views of steps in one of the present embodiments of a process for coating the sensor of FIG. 2.
Figure 10:
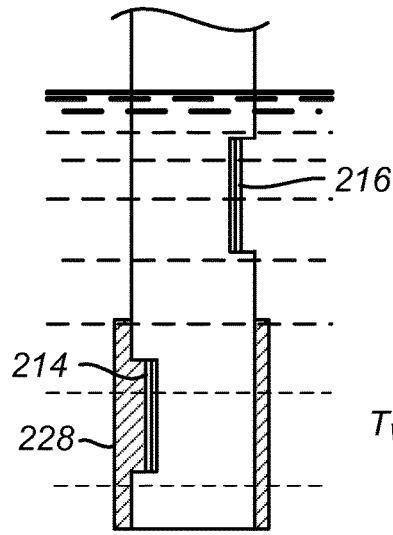

To solve this problem, the present embodiments provide a dipping process with a variable withdrawal rate to control the thickness of the membrane system at different locations on the sensor 200. For example, with reference to FIG. 9, the sensor 200 is dipped in an enzyme solution 240 up to a point that lies between the WE 214 and the NE 216. This step applies the enzyme layer 228 (FIG. 4) to the WE 214, but not to the NE 216. The sensor 200 is then withdrawn at a first rate. With reference to FIG. 10, the sensor 200 is then dipped in a non-enzyme solution 244 up to a point above the NE 216. This step applies the non-enzyme layer 230 (FIG. 5) to both the WE 214 and the NE 216. The withdrawal from the non-enzyme solution 244 has a variable rate, such as a first rate until the NE 216 emerges from the dip solution 244, then a second faster rate until the WE 214 emerges from the dip solution 244. For example, one embodiment of a dip process may be as follows:

Optional underlayer (e.g., electrode and/or interference) application (one withdrawal rate at both electrodes 214, 216);

Enzyme layer 228 application (one withdrawal rate only at WE 214);

Non-enzyme layer 230 application (faster withdrawal rate at WE 214 than at NE 216); and Resistance layer application (one withdrawal rate at both electrodes 214, 216).

Figure 11:
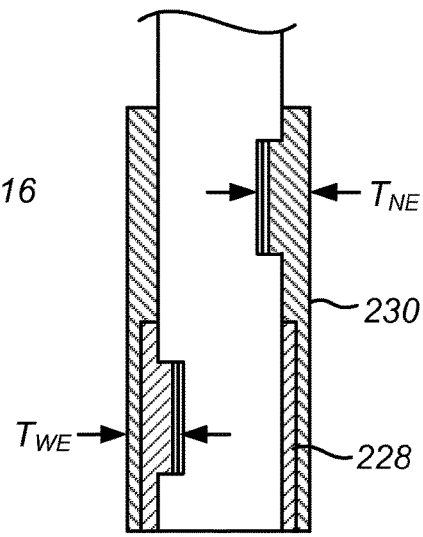
FIG. 11 is a schematic side elevation of the sensor of FIG. 2 coated according to the process of FIGS. 9 and 10.

The foregoing process yields a thicker non-enzyme layer 230 over the NE 216 than over the WE 214. The thicker non-enzyme layer 230 compensates for the extra layer (enzyme) over the WE 214. By precisely controlling the dip parameters, including the withdrawal rate, the thickness of the membrane system over the WE 214, $T_{WE}$, can be made to be substantially equal to the thickness of the membrane system over the NE 216, $T_{NE}$, as shown in FIG. 11. For example, the variance in thickness may be as small as 1 µm, or 2 µm, or 3 µm, or 4 µm, or 5 µm. The substantially equal thicknesses $T_{WE}$, $T_{NE}$, normalize the behavior of the membrane system in the two locations, particularly with regard to permeability of analyte. Preferably, the permeability of the membrane system over the WE 214 is within 5%, 4%, 3%, 2%, or 1% of the permeability of the membrane system over the NE 216.

Figure 11A:
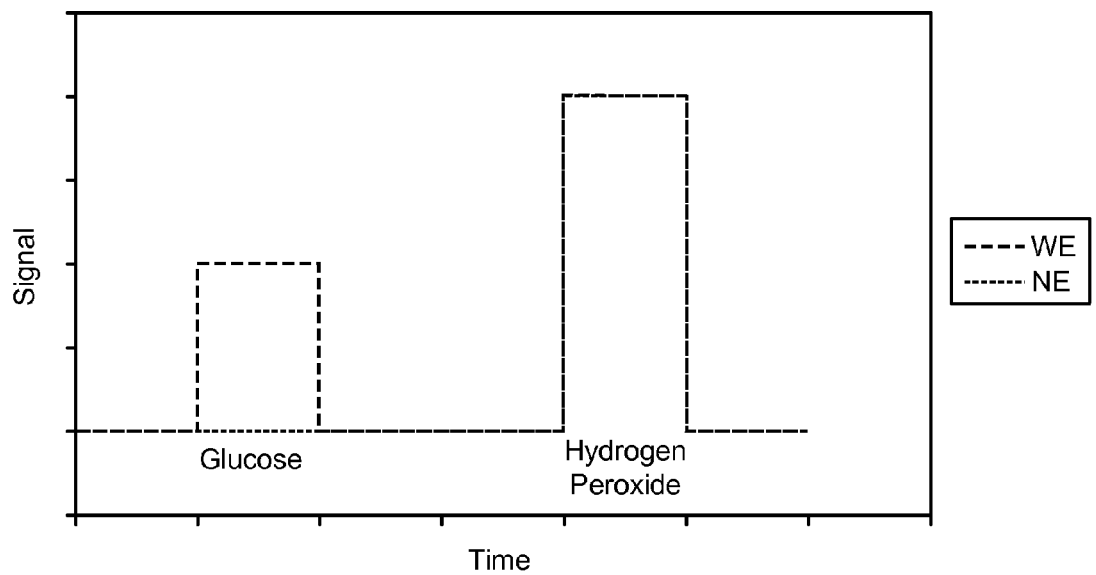
FIGS. 11A and 11B are graphs showing sensor signals in response to different measurable species.
Figure 11B:
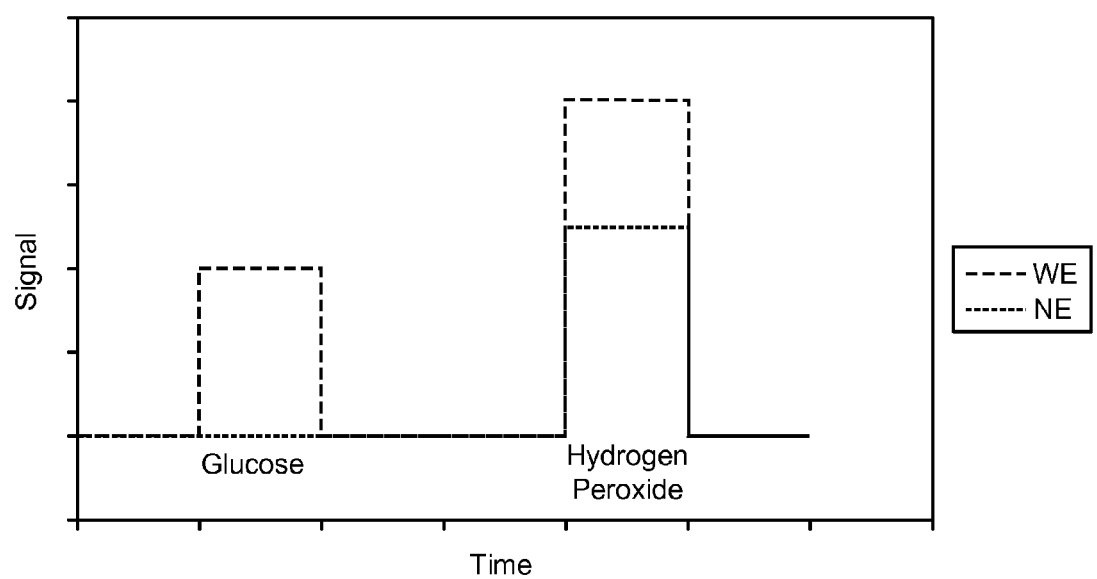

FIGS. 11A and 11B illustrate one example of a test for determining whether the permeability of the membrane system over the WE 214 is substantially the same as the permeability of the membrane system over the NE 216. These figures plot sensor signal versus time for a sensor having a WE and a NE. The measured signal from the WE is shown with coarsely dashed lines, and the measured signal from the NE is shown with finely dashed lines.

In FIG. 11A, the permeability of the membrane system over the WE 214 is substantially the same as the permeability of the membrane system over the NE 216. The sensor is dipped first in a solution containing glucose (signal bar on left), and second in a solution containing hydrogen peroxide (signal bar on right). Although hydrogen peroxide is shown here, any other small molecule measureable species other than glucose, capable of diffusing through the membrane, may be used to measure permeability of the membrane system, including but not limited to acetaminophen, ascorbic acid and uric acid. When dipped in glucose solution, the WE provides a measurable signal, while the NE does not, because the enzyme in the WE reacts with the glucose, while the NE has no enzyme. When dipped in hydrogen peroxide, both sensors provide a signal of the same magnitude, because both have the same permeability.

In FIG. 11B, the permeability of the membrane system over the WE 214 is greater than the permeability of the membrane system over the NE 216. Again, the sensor is dipped first in a solution containing glucose (signal bar on left), and second in a solution containing hydrogen peroxide (signal bar on right), or any other measureable species other than glucose. When dipped in glucose, the WE again provides a measurable signal, while the NE does not. When dipped in hydrogen peroxide, the WE provides a signal of greater magnitude than that of the NE, because permeability of the membrane system over the WE is greater than the permeability of the membrane system over the NE. In some embodiments, the permeabilities of the membrane systems may be considered to be substantially the same if they are within 10% of one another, or in some cases within 5%. In other embodiments, one standard for administering the test illustrated in FIGS. 11A and 11B is EP7-A2 (interference testing in clinical chemistry—approved guideline), which is incorporated by reference herein.

Figure 12:
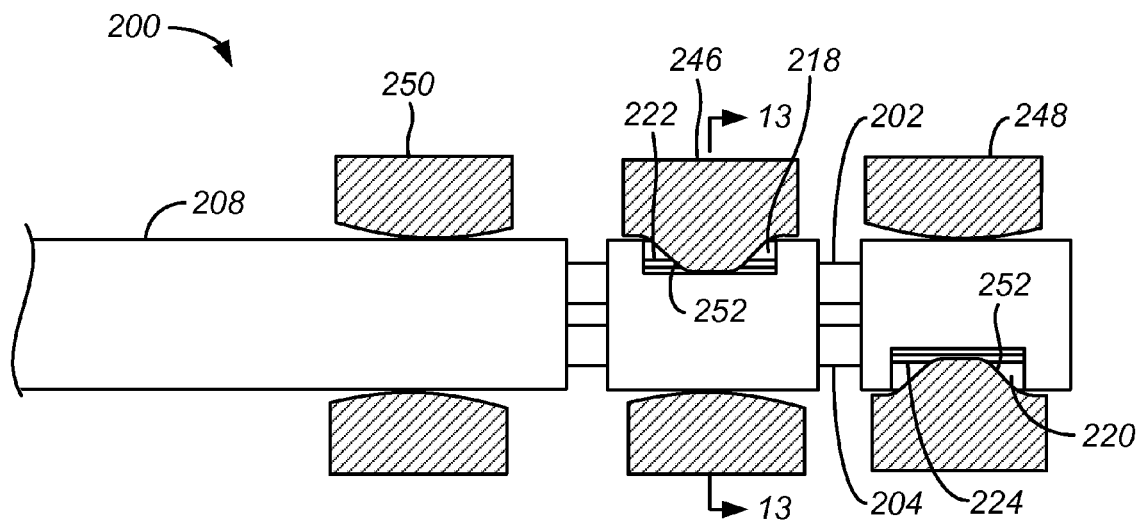
FIG. 12 is a schematic side elevation view of another of the present embodiments of a continuous analyte sensor.
Figure 13:
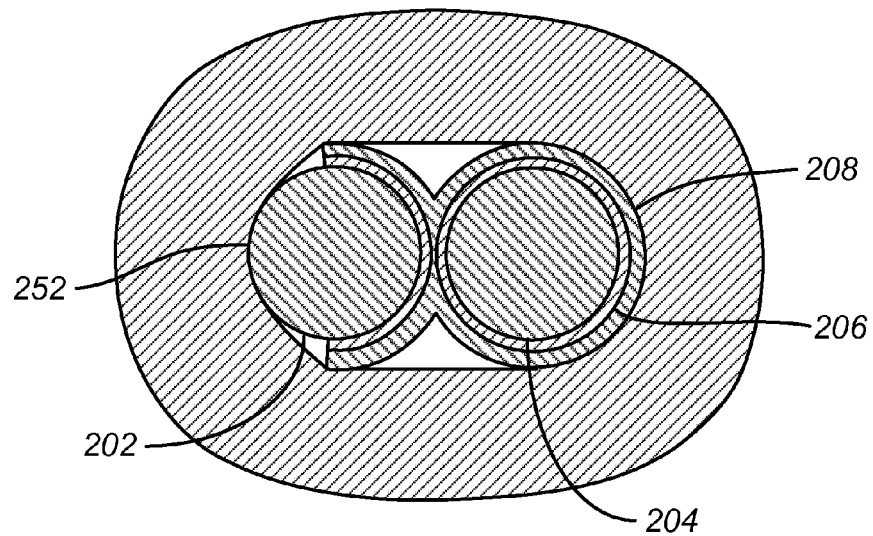
FIG. 13 is a schematic cross-sectional view of the sensor of FIG. 12 taken along the line 13-13.

With reference to FIGS. 12 and 13, another of the present embodiments comprises apparatus and methods for electrically connecting the sensor 200 of FIG. 2 to sensor 200 electronics (not shown). With reference to FIG. 12, and as discussed above, the material covering approximately half of the diameter of each wire 202, 204 is removed to create third and fourth windows 218, 220. All of the material covering the wires 202, 204 in the third and fourth windows 218, 220 is removed to expose the bare wires 202, 204. The wires 202, 204 in the third and fourth windows 218, 220 thus comprise electrical contacts 222, 224. While in the illustrated embodiment the material covering approximately half of the diameter of each wire 202, 204 is removed, in an alternative embodiment the material covering each wire 202, 204 may be removed over the entire circumference of the wire 202, 204.

Figure 14:
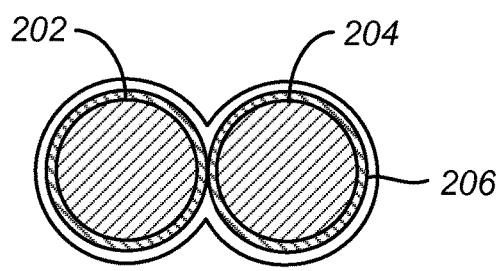
FIG. 14 is a schematic cross-sectional view of the sensor of FIG. 2 taken along the line 14-14.

With reference to FIGS. 12 and 14, on either side of the third window 218, bands of the material covering the wire 202, 204 are removed (in part or in whole). The bands of material removed comprise all material layers other than the insulator 206. The bare wires 202, 204 are thus not exposed in the area of the removed bands. However, the removed material includes the outer conductive layer 208 and any membrane 226 that may be present. Removing the outer conductive layer 208 electrically isolates the contacts 222, 224 from one another and from the working electrodes 214, 216. Processes for removing the material layers are described above and will not be repeated here.

First and second bands 246, 248, also referred to as "pucks," encircle the first and second contacts 222, 224, respectively. A third puck 250 encircles the outer conductive layer 208 in the area spaced from the contacts 222, 224. Each puck 246, 248, 250 comprises an elastomeric conductive material, such as silicone rubber filled with carbon particles.

For both the WE 214 and the NE 216, a corresponding one of the first and second pucks 246, 248 contacts the bare surface of the respective electrode wire 202, 204. Each of the pucks 246, 248 thus provides a surface for receiving electrical connections to sensor electronics (not shown). The large contact area between the pucks 246, 248 and the wires 202, 204 provides excellent electrical connection with low resistance. The third puck 250 contact with the conductive layer 208 and serves as a reference electrode.

With reference to FIGS. 12 and 13, each of the elastomeric conductive bands 246, 248 includes a radially inwardly directed bulge 252 that contacts a respective one of the wires 202, 204. The bulge 252 results from the elasticity of the pucks 246, 248 and the relative dimensions of the pucks 246, 248 and the sensor 200. An inner diameter of each puck 246, 248 is preferably smaller that the outer diameter of the sensor 200 in the areas of the conductive outer layer 208. Thus, when each puck 246, 248 is positioned around the sensor 200 in the areas of the windows 218, 220, outer portions of each puck 246, 248 are restrained by the relatively larger outer diameter of the outer conductive layer 208, while a central portion of each puck 246, 248 is able to relax and bulge inward in the area of each window 218, 220, which has a relatively smaller outer diameter than the outer conductive layer 208. Alternatively, or in addition to the inward bulge 252, a conductive paste (not shown) may be disposed between the elastomeric conductive bands 246, 248 and their respective wires 202, 204. The conductive paste may, for example, comprise silver chloride.

Advantageously, the sensor 200 illustrated in FIG. 12 includes longitudinally spaced contacts 222, 224 positioned about a common axis. This arrangement reduces the profile of the sensor 200, enabling it to fit within the lumen of a fine gauge introducer needle without the need to provide a channel in the sidewall of the needle. In an alternative embodiment, the pucks 246, 248 may be omitted, and instead the third and fourth windows 218, 220 are aligned with electrical contacts (not shown).

FIGS. 14A through 14D are schematic side cross-sectional views that illustrate components of a sensor applicator and their cooperating relationships at various stages of sensor insertion in one embodiment. FIG. 14A illustrates the needle and sensor loaded prior to sensor insertion. FIG. 14B illustrates the needle and sensor after sensor insertion. FIG. 14C illustrates the sensor and needle during needle retraction. FIG. 14D illustrates the sensor remaining within the contact subassembly after needle retraction. Although the embodiments described herein suggest manual insertion and/or retraction of the various components, one or more of the stages could be automated. For example, spring-loaded mechanisms that can be triggered to automatically insert and/or retract the sensor, needle, or other cooperative applicator components can be implemented.

Referring to FIG. 14A, the sensor 254 is shown disposed within the needle 256, which is disposed within an optional cannula 258. In this embodiment, the cannula 258 is provided to maintain an opening within the contact pucks 246, 248, 250 to provide low friction between the needle 256 and the contact pucks during insertion and retraction of the needle 256. However, the cannula is an optional component, which can be advantageous in some embodiments wherein the contact pucks 246, 248, 250 are formed from an elastomer or other material with a relatively high friction coefficient, and which can be omitted in other embodiments wherein the contact pucks are formed from a material with a relatively low friction coefficient (for example, hard plastic or metal). A cannula, or the like, can be preferred in embodiments wherein the contact pucks 246, 248, 250 are formed from a material designed to frictionally hold the sensor 200 (see FIG. 14D), for example, by the relaxing characteristics of an elastomer, or the like. In these embodiments, the cannula is provided to ease insertion of the needle through the contacts, while allowing for a frictional hold of the contacts on the sensor 200 upon subsequent needle retraction. Stabilization of the sensor in or on the contact pucks is described in more detail with reference to FIG. 14D. Although FIG. 14A illustrates the needle and sensor inserted into the contact pucks as the initial loaded configuration, alternative embodiments contemplate a step of loading the needle through the cannula 258 and/or contact pucks prior to sensor insertion.

Referring to FIG. 14B, the sensor 200 and needle 256 are shown in an extended position. In this stage, the pushrod 264 has been forced to a forward position. The pushrod 264 is designed to cooperate with other components of the applicator to ensure that the sensor 200 extends to the forward position simultaneously within the needle 256.

Referring to FIG. 14C, the needle 256 is shown during the retraction process. In this stage, the pushrod 264 is held in its extended (forward) position in order to maintain the sensor 200 in its extended (forward) position until the needle 256 has substantially fully retracted from the contact pucks. Simultaneously, the cooperating applicator components retract the needle 256 and cannula 258 backward by a pulling motion (manual or automated) thereon. In preferred embodiments, a cannula carrier (not shown) engages with cooperating applicator components such that a backward (retraction) motion applied to the cannula carrier retracts the needle 256 and cannula 258, without (initially) retracting the pushrod 264. In an alternative embodiment, the pushrod 264 can be omitted and the sensor 200 held it its forward position by a cam, elastomer, or the like, which is in contact with a portion of the sensor while the needle moves over another portion of the sensor. One or more slots can be cut in the needle to maintain contact with the sensor during needle retraction.

Referring to FIG. 14D, the needle 256, cannula 258, and pushrod 264 are all retracted from contact pucks, leaving the sensor 200 disposed therein. The cooperating applicator components are designed such that when the needle 256 has substantially cleared from the contact pucks, the pushrod 264 is retracted along with the needle 256 and cannula 258. The applicator can then be released (manually or automatically) from the contacts 262.

The preferred embodiments are designed to ensure a retention force that retains the sensor 200 within a mounting unit (not shown) that holds the contact pucks and ensures stable electrical connection of the sensor 200 and its associated contacts 246, 248, 250. Although the illustrated embodiments and associated text describe the sensor 200 extending through the contact pucks to form an interference fit therein, a variety of alternatives are contemplated by the inventors. In one alternative embodiment, the sensor is configured to be disposed adjacent to the contacts (rather than between the contacts). The contacts can be constructed in a variety of known configurations, for example, metallic contacts, cantilevered fingers, pogo pins, or the like, which are configured to press against the sensor after needle retraction.

Figure 15:
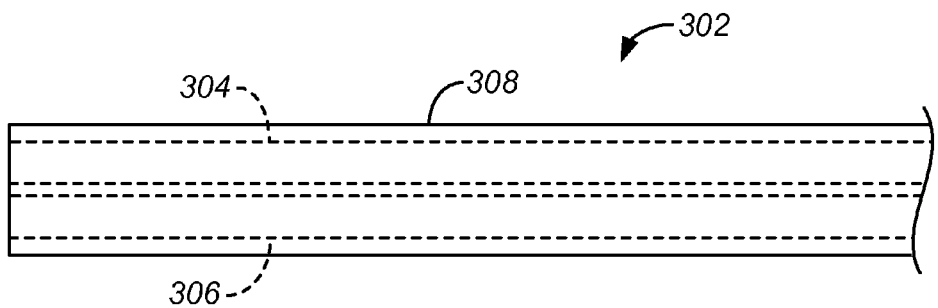
FIG. 15 is a schematic side elevation view of a bifilar wire.
Figure 16:
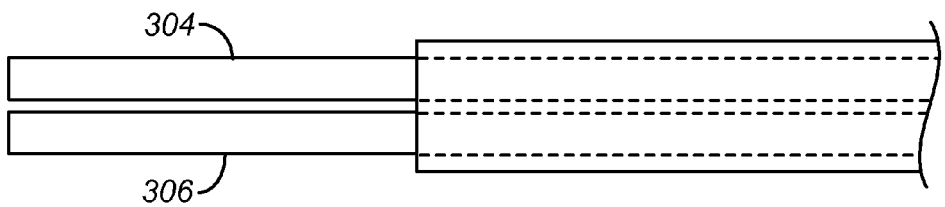
FIG. 16 is a schematic side elevation view of the bifilar wire of FIG. 15 with outer layers removed.
Figure 17:
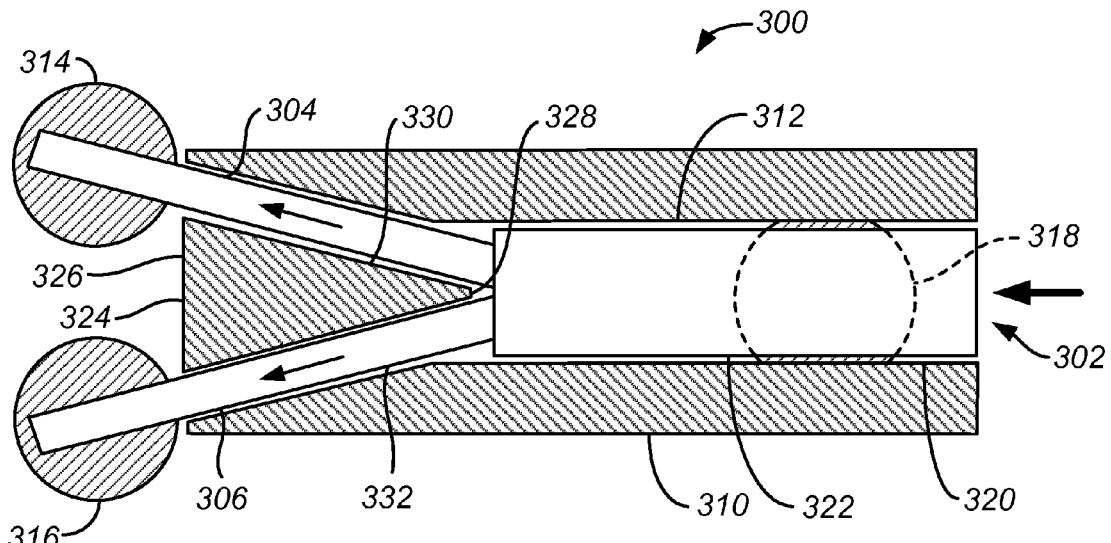
FIG. 17 is a schematic side elevation view of the bifilar wire of FIG. 16 in combination with a base structure, according to the present embodiments.

FIGS. 15-17 illustrate one embodiment of a bifilar, three electrode sensor 300 and method of making. In the method of making, a bifilar wire 302 (FIG. 15) includes first and second wires 304, 306 coated with an insulator (not shown), and an outer conductive layer 308 around the insulator 206. The outer conductive layer 308 may comprise silver chloride, or any other conductive material. The bifilar wire 302 may be similar in structure and/or materials to the bifilar wire describe with respect to FIG. 2.

With reference to FIG. 16, the outer conductive layer 308 and the insulator are stripped from the wires 304, 306 over a length at the proximal ends of the wires 304, 306, leaving two separated bare wires 304, 306. Processes for removing the material layers are described above and will not be repeated here. However, for cost effectiveness and ease of handling, this operation may be performed using a reel-to-reel process in series with removal of the working electrode windows and/or contact windows described above with respect to FIG. 2.

With reference to FIG. 17, the stripped wires 304, 306 are combined with a base structure 310. The base 310 includes an interior guide channel 312 and three contacts 314, 316, 318. The guide channel 312 includes a distal portion 320 having a size and cross-sectional shape configured to receive the non-stripped portion 322 of the bifilar wire 302. At a proximal end 324, the base 310 includes a separator 326, which comprises a peak 328 at a distal end, and opposing ramped surfaces 330, 332 that extend diagonally away from the peak 328. When the bifilar wire 302 is inserted into the guide channel 312 in the direction of the arrows, with the stripped wires 304, 306 at the leading end, the proximal ends of the wires 304, 306 contact the ramped surfaces 330, 332 and are thus separated from one another as the bifilar wire 302 is advanced farther and the wires 304, 306 continue to advance up the ramped surfaces 330, 332. Upon full insertion, the two wires 304, 306 are aligned with two of the contacts 314, 316 at the proximal end 324 of the base 310, while the outer conductive layer 308 is aligned with a third one of the contacts 318 at the distal end of the base 310. Electrical connection with the contacts 314, 316, 318 can be achieved by pressing the wires 304, 306 against the contacts

314, 316, 318 using structures provided in the base 310. For example, elastomeric pucks similar to those described with respect to FIGS. 12 and 13 can be provided. Alternatively, the wires 304, 306 can be secured to the contacts 314, 316, 318 using electrically conductive epoxy, or any other technique.

The bifilar, three electrode sensor 300 shown in FIG. 17 advantageously provides three contacts 314, 316, 318, where conventional wire-based sensors provide only two contacts. The base structure 310, with the ramped separator 326, reduces manual alignment steps when assembling the stripped wire 302 with the base 310, thus facilitating efficient assembly.

Methods and devices that are suitable for use in conjunction with aspects of the preferred embodiments are disclosed in U.S. Pat. No. 4,757,022; U.S. Pat. No. 4,994,167; U.S. Pat. No. 6,001,067; U.S. Pat. No. 6,558,321; U.S. Pat. No. 6,702,857; U.S. Pat. No. 6,741,877; U.S. Pat. No. 6,862,465; U.S. Pat. No. 6,931,327; U.S. Pat. No. 7,074,307; U.S. Pat. No. 7,081,195; U.S. Pat. No. 7,108,778; U.S. Pat. No. 7,110,803; U.S. Pat. No. 7,134,999; U.S. Pat. No. 7,136,689; U.S. Pat. No. 7,192,450; U.S. Pat. No. 7,226,978; U.S. Pat. No. 7,276,029; U.S. Pat. No. 7,310,544; U.S. Pat. No. 7,364,592; U.S. Pat. No. 7,366,556; U.S. Pat. No. 7,379,765; U.S. Pat. No. 7,424,318; U.S. Pat. No. 7,460,898; U.S. Pat. No. 7,467,003; U.S. Pat. No. 7,471,972; U.S. Pat. No. 7,494,465; U.S. Pat. No. 7,497,827; U.S. Pat. No. 7,519,408; U.S. Pat. No. 7,583,990; U.S. Pat. No. 7,591,801; U.S. Pat. No. 7,599,726; U.S. Pat. No. 7,613,491; U.S. Pat. No. 7,615,007; U.S. Pat. No. 7,632,228; U.S. Pat. No. 7,637,868; U.S. Pat. No. 7,640,048; U.S. Pat. No. 7,651,596; U.S. Pat. No. 7,654,956; U.S. Pat. No. 7,657,297; U.S. Pat. No. 7,711,402; U.S. Pat. No. 7,713,574; U.S. Pat. No. 7,715,893; U.S. Pat. No. 7,761,130; U.S. Pat. No. 7,771,352; U.S. Pat. No. 7,774,145; U.S. Pat. No. 7,775,975; U.S. Pat. No. 7,778,680; U.S. Pat. No. 7,783,333; U.S. Pat. No. 7,792,562; U.S. Pat. No. 7,797,028; U.S. Pat. No. 7,826,981; U.S. Pat. No. 7,828,728; U.S. Pat. No. 7,831,287; U.S. Pat. No. 7,835,777; U.S. Pat. No. 7,857,760; U.S. Pat. No. 7,860,545; U.S. Pat. No. 7,875,293; U.S. Pat. No. 7,881,763; U.S. Pat. No. 7,885,697; U.S. Pat. No. 7,896,809; U.S. Pat. No. 7,899,511; U.S. Pat. No. 7,901,354; U.S. Pat. No. 7,905,833; U.S. Pat. No. 7,914,450; U.S. Pat. No. 7,917,186; U.S. Pat. No. 7,920,906; U.S. Pat. No. 7,925,321; U.S. Pat. No. 7,927,274; U.S. Pat. No. 7,933,639; U.S. Pat. No. 7,935,057; U.S. Pat. No. 7,946,984; U.S. Pat. No. 7,949,381; U.S. Pat. No. 7,955,261; U.S. Pat. No. 7,959,569; U.S. Pat. No. 7,970,448; U.S. Pat. No. 7,974,672; U.S. Pat. No. 7,976,492; U.S. Pat. No. 7,979,104; U.S. Pat. No. 7,986,986; U.S. Pat. No. 7,998,071; U.S. Pat. No. 8,000,901; U.S. Pat. No. 8,005,524; U.S. Pat. No. 8,005,525; U.S. Pat. No. 8,010,174; U.S. Pat. No. 8,027,708; U.S. Pat. No. 8,050,731; U.S. Pat. No. 8,052,601; U.S. Pat. No. 8,053,018; U.S. Pat. No. 8,060,173; U.S. Pat. No. 8,060,174; U.S. Pat. No. 8,064,977; U.S. Pat. No. 8,073,519; U.S. Pat. No. 8,073,520; U.S. Pat. No. 8,118,877; U.S. Pat. No. 8,128,562; U.S. Pat. No. 8,133,178; U.S. Pat. No. 8,150,488; U.S. Pat. No. 8,155,723; U.S. Pat. No. 8,160,669; U.S. Pat. No. 8,160,671; U.S. Pat. No. 8,167,801; U.S. Pat. No. 8,170,803; U.S. Pat. No. 8,195,265; U.S. Pat. No. 8,206,297; U.S. Pat. No. 8,216,139; U.S. Pat. No. 8,229,534; U.S. Pat. No. 8,229,535; U.S. Pat. No. 8,229,536; U.S. Pat. No. 8,231,531; U.S. Pat. No. 8,233,958; U.S. Pat. No. 8,233,959; U.S. Pat. No. 8,249,684; U.S. Pat. No. 8,251,906; U.S. Pat. No. 8,255,030; U.S. Pat. No. 8,255,032; U.S. Pat. No. 8,255,033; U.S. Pat. No. 8,257,259; U.S. Pat. No. 8,260,393; U.S. Pat. No. 8,265,725; U.S. Pat. No. 8,275,437; U.S. Pat. No. 8,275,438; U.S. Pat. No. 8,277,713; U.S. Pat. No. 8,280,475; U.S. Pat. No. 8,282,549; U.S. Pat. No. 8,282,550; U.S. Pat. No. 8,285,354; U.S. Pat. No. 8,287,453; U.S. Pat. No. 8,290,559; U.S. Pat. No. 8,290,560; U.S. Pat. No. 8,290,561; U.S. Pat. No. 8,290,562; U.S. Pat. No. 8,292,810; U.S. Pat. No. 8,298,142; U.S. Pat. No. 8,311,749; U.S. Pat. No. 8,313,434; U.S. Pat. No. 8,321,149; U.S. Pat. No. 8,332,008; U.S. Pat. No. 8,346,338; U.S. Pat. No. 8,364,229; U.S. Pat. No. 8,369,919; U.S. Pat. No. 8,374,667; U.S. Pat. No. 8,386,004; and U.S. Pat. No. 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-

A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-

0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; and U.S. Patent Publication No. 2005-0182451-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS"; U.S. application Ser. No. 13/779,607 filed on Feb. 27, 2013 and entitled "ZWITTERION SURFACE MODIFICATIONS FOR CONTINUOUS SENSORS"; U.S. application Ser. No. 13/780,808 filed on Feb. 28, 2013 and entitled "SENSORS FOR CONTINUOUS ANALYTE MONITORING, AND RELATED METHODS"; and U.S. application Ser. No. 13/784,523 filed on Mar. 4, 2013 and entitled "ANALYTE SENSOR WITH INCREASED REFERENCE CAPACITY".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. An analyte sensor, comprising:
    a first working electrode, wherein the first working electrode is an enzyme electrode;
    a second working electrode, wherein the second working electrode is a non-enzyme electrode; and
    a membrane system overlying the first working electrode and the second working electrode, wherein the membrane system comprises a first portion over the first working electrode and a second portion over the second working electrode, wherein a permeability to hydrogen peroxide of the membrane system over the first working electrode is greater than a permeability to hydrogen peroxide of the membrane system over the second working electrode, and wherein the permeability to hydrogen peroxide of the membrane over the first working electrode and the permeability to hydrogen peroxide of the membrane system over the second working electrode are different by more than 5%.

2. The analyte sensor of claim 1, wherein the first portion is cross-linked.

3. The analyte sensor of claim 2, wherein the second portion is cross-linked, and the first portion is cross-linked by an amount different from the other portions.

4. The analyte sensor of claim 1, wherein the first portion has a lower content of a hydrophilic species than the second portion.

5. The analyte sensor of claim 4, wherein the hydrophilic species is removed by a secondary removal process, a leaching process, or a precipitation process involving heat, pH, or solvents.

6. The analyte sensor of claim 1, wherein the first portion comprises a scavenging material, the scavenging material configured to scavenge at least a portion of a byproduct of a chemical reaction occurring at the first working electrode between an analyte and a reactant.

7. The analyte sensor of claim 6, wherein the byproduct comprises hydrogen peroxide.

8. The analyte sensor of claim 6, wherein the scavenging material comprises peroxidase or catalase.

9. The analyte sensor of claim 6, wherein the scavenging material is deposited on the sensor using masking followed by dipping, or by selective spraying.

10. The analyte sensor of claim 1, wherein the first portion comprises an interruption in the membrane properties.

11. The analyte sensor of claim 1, wherein the first portion comprises a mechanical ring that encircles a membrane portion.

12. The analyte sensor of claim 1, wherein the first working electrode is located on a first wire, the second working electrode is located on a second wire, and the first and second wires are non-concentric.

13. The analyte sensor of claim 1, wherein the analyte sensor is a continuous analyte sensor configured to continuously measure analyte concentration.

14. The analyte sensor of claim 1, wherein the analyte sensor is a glucose sensor.

15. The analyte sensor of claim 1, wherein the analyte sensor is a continuous glucose sensor configured to continuously measure glucose concentration.

16. The analyte sensor of claim 1, wherein the permeability to hydrogen peroxide of the membrane over the first working electrode and the permeability to hydrogen peroxide of the membrane system over the second working electrode are different by more than 10%.

17. The analyte sensor of claim 1, wherein the permeability to hydrogen peroxide of the membrane over the first working electrode and the permeability to hydrogen peroxide of the membrane system over the second working electrode are different by about 60% or less.

18. The analyte sensor of claim 16, wherein the permeability to hydrogen peroxide of the membrane over the first working electrode and the permeability to hydrogen peroxide of the membrane system over the second working electrode are different by about 60% or less.

* * * * *